United States Patent [19]

Tulley

[11] Patent Number: 5,441,872
[45] Date of Patent: Aug. 15, 1995

[54] METHOD FOR THE ANALYSIS OF VITAMIN C

[75] Inventor: Richard T. Tulley, Baton Rouge, La.

[73] Assignee: Board of Supervisors of Louisiana State University and Agricultural and Mechanical College, Baton Rouge, La.

[21] Appl. No.: 72,595

[22] Filed: Jun. 4, 1993

[51] Int. Cl.$^6$ .................. C12Q 1/26; C12Q 1/28; C12C 1/00; C12N 1/00
[52] U.S. Cl. ...................... 435/25; 435/28; 435/4; 435/962; 435/968; 436/93; 436/91; 436/24; 436/800; 436/825; 426/252; 426/102; 426/330.5; 426/333; 426/331; 426/616
[58] Field of Search ............ 435/25, 28, 14, 274, 435/4, 962, 968; 436/66, 80, 92, 93, 91, 74, 800, 825; 424/1.1; 426/252, 102, 330.5, 333, 331, 616

[56] References Cited

U.S. PATENT DOCUMENTS

| | | | |
|---|---|---|---|
| 4,028,465 | 6/1977 | Lewin et al. | 436/505 |
| 4,152,116 | 5/1979 | Deneke et al. | 436/93 |
| 4,160,696 | 7/1979 | Wu | 435/25 |
| 4,179,445 | 12/1979 | Sieb et al. | 435/25 |
| 4,288,541 | 9/1981 | Magers et al. | 435/14 |
| 4,327,183 | 4/1982 | Masuda et al. | 435/274 |
| 4,780,549 | 10/1988 | Terao et al. | 549/315 |
| 5,004,493 | 4/1991 | Norris | 71/88 |
| 5,079,140 | 1/1992 | Albarella et al. | 436/80 |
| 5,212,096 | 5/1993 | Kolhouse et al. | 436/96 |
| 5,264,348 | 11/1993 | Schick et al. | 436/73 |

OTHER PUBLICATIONS

Vuilleumier et al, Jour of Micronutrient Analysis 5 (1989) 25–34.
Deutsch et al, Jour. of The A.O.Ac. (vol. 48, No. 6, 1965). pp. 1248–1256. (1965).
Roy et al, Jour. of The A.O.A.C. (vol. 59, No. 6, 1976). pp. 1244–1250.
Pachla et al., "Analytical Methods for Determining Ascorbic Acid in Biological Samples, Food Products, and Pharmaceuticals," J. Assoc. Off. Anal. Chem., vol. 68, No. 1, pp. 1–12 (1985).
Liu et al., "Specific Spectrophotometry of Ascorbic Acid in Serum or Plasma by Use of Ascorbate Oxidase," Clin. Chem., vol. 28, No. 11, pp. 2225–2228 (1982).
Kirk et al., "Fluorometric Assay for Total Vitamin C Using Continuous Flow Analysis," J. Food Sci., vol. 40, pp. 463–466 (1975).
Egberg et al., "Semiautomated Method for the Fluorometric Determination of Total Vitamin C in Food Products," J. Assoc. Off. Anal. Chem., vol. 60, No. 1, pp. 126–131 (1977).

Primary Examiner—Michael G. Wityshyn
Assistant Examiner—Louise N. Leary
Attorney, Agent, or Firm—John H. Runnels

[57] ABSTRACT

A new enzymatic rate method is disclosed for the analysis of Vitamin C using ascorbate oxidase. Total Vitamin C can be measured in a single analysis, in a procedure amenable to automation. Any dehydroascorbic acid (DHAA) in the sample is reduced to ascorbic acid. Then a coupling agent such as o-phenylenediamine (OPDA) is added to the sample, and any nonspecific reactions with, or spectrometric interferences from, other components of the sample are measured, to be blanked out from the final measurement. Then ascorbate oxidase is added, oxidizing ascorbic acid to DHAA; the DHAA then reacts with the OPDA already present from the prior step, and the quinoxaline derivative product may be measured spectrometrically, e.g., by absorbance at 350 nm.

14 Claims, No Drawings

METHOD FOR THE ANALYSIS OF VITAMIN C

The development of this invention was partially funded by the Government under Grant DAMD-17-88-Z-8023 from the U.S. Army Research and Development Command. The Government may have certain rights in this invention.

This invention pertains to a method for the analysis of Vitamin C, particularly to a method for the analysis of Vitamin C which may readily be automated.

There exists an unfulfilled need for an accurate, rapid, easy-to-implement, automatable method for measuring the amount of Vitamin C in a sample. The need to make such measurements exists in vitamin supplement manufacturing, in the processed foods industry, in the pharmaceutical industry, and in clinical medicine and nutrition. In manufacturing vitamin supplements and processed foods, it is frequently important for the manufacturer to have an accurate assay of the amount of Vitamin C present in the product. In clinical medicine and nutrition, measurements of a patient's plasma Vitamin C levels can be important for a number of reasons, including nutritional evaluations and deficiency (i.e., scurvy) diagnosis. Vitamin C has a number of biological functions, including anti-oxidant activity, a role in the metabolism of several biologically important compounds, a role in immune function, and a possible role in anti-cancer activity.

Difficulties encountered by prior methods for the analysis of Vitamin C include lack of specificity, difficulty in automation, the use of corrosive reagents, and/or the need for double reaction schemes due to interferences from other substances. Liquid chromatographic methods have demonstrated good sensitivity and specificity, but their implementation requires specialized equipment; the procedures may be rather lengthy; and such methods are difficult to automate. O-phenylenediamine (OPDA) has been used as a coupling reagent for the spectrometric analysis of ascorbic acid (AA). However, because OPDA reacts with dehydroascorbic acid (DHAA) and other substances, prior methods have used non-specific oxidizing agents to generate DHAA from AA.

Vuilleumier et al., "Fluorometric Assay of Vitamin C in Biological Materials Using a Centrifugal Analyser with Fluorescence Attachment," J. Micronutrient Analysis., vol. 5, pp. 25–34 (1989) discusses a method of assaying Vitamin C comprising the sequential steps of: first, reaction with metaphosphoric acid; second, enzymatic oxidation with ascorbate oxidase; and third, coupling with o-phenylenediamine.

The Vuilleumier technique is subject to interference from other substances which react with OPDA to form quinoxalines. One such substance is pyruvic acid or pyruvate. See Deutsch et al., "Microfluorometric Assay for Vitamin C," J. Assoc. Off. Anal. Chem., vol. 48, No. 6, pp. 1248–56 (1965). Interference from pyruvic acid or pyruvate is a substantial problem, as pyruvate is present in many biological substances. Other naturally occurring compounds may also present chemical or spectrometric interferences in the Vuilleumier process.

Other prior methods of determining ascorbic acid are discussed in Pachla et al., "Analytical Methods for Determining Ascorbic Acid in Biological Samples, Food Products, and Pharmaceuticals," J. Assoc. Off. Anal. Chem., vol. 68, No. 1, pp. 1–12 (1985); Liu et al., "Specific Spectrophotometry of Ascorbic Acid in Serum or Plasma by Use of Ascorbate Oxidase," Clin. Chem., vol. 28, no. 11, pp. 2225–28 (1982); Roy et al., "Automated Fluorometric Method for the Determination of Total Vitamin C in Food Products," J. Assoc. Off. Anal. Chem., vol. 59, no. 6, pp. 1244–50 (1976); Kirk et al., "Fluorometric Assay for Total Vitamin C Using Continuous Flow Analysis," J. Food Sci., vol. 40, pp. 463–66 (1975); and Egberg et al., "Semiautomated Method for the Fluorometric Determination of Total Vitamin C in Food Products," J. Assoc. Off. Anal. Chem., vol. 60, no. 1, pp. 126–131 (1977).

These and other disadvantages in analyzing Vitamin C have been overcome by the present invention. A new enzymatic rate method has been discovered for the analysis of Vitamin C using ascorbate oxidase (AO) (EC 1.10.3.3). The novel method permits total Vitamin C to be measured in a single analysis, with an easy-to-perform correction for interferences from other substances. The novel method has been successfully automated on a Beckman Synchron CX5 automated chemistry analyzer.

In the novel method of this invention, the sample is first reacted with a deproteinizing agent such as metaphosphoric acid (MPA), and a reducing agent such as dithiothreitol (DTT). The DTT reduces DHAA to ascorbic acid. Then a coupling agent such as o-phenylenediamine (OPDA) is added, converting nonspecific reactants to product; the absorbance or fluorescence of the products (and any other sample components) at a characteristic wavelength (such as 350 nm) is measured, a measurement to be blanked out of the final calculation. In the third step, ascorbate oxidase (AO) is added, catalyzing the oxidation of ascorbic acid to DHAA; the DHAA couples with the OPDA or other coupling agent already present in the reaction mixture to give a quinoxaline product—in the case of OPDA, the product is 3-(1,2-dihydroxyethyl)furo[3,4-b]quinoxaline-1-one; and absorbance or fluorescence at the same wavelength is again measured, with the previous blank measurement subtracted out. In this manner, potential chemical and spectrometric interferences are minimized or eliminated.

Any deproteinizing agent which does not adversely affect the outcome of the measurements will work in the place of MPA. Exemplary of deproteinizing agents are trichloroacetic acid, sulfosalicylic acid, perchloric acid, oxalic acid, acetic acid, formic acid, and an ultrafilter to remove proteins through ultrafiltration.

Any reducing agent which does not adversely affect the outcome of the measurements will work in place of DTT. Exemplary of reducing agents are glutathione; mercaptoethanol; cysteine; homocysteine; and 2,3-dimercapto-1-propanol.

Other coupling agents permitting the spectroscopic identification of DHAA will work in place of OPDA. Exemplary are substituted 1,2-diaminobenzenes, such as 1,2-diamino-4,5-dimethylbenzene; 1,2-diamino-4-methoxybenzene; and 1,2-diamino-4-ethoxybenzene.

Other spectroscopic identification means for identifying the coupled reaction product will readily occur to one of ordinary skill in the art. For example, when OPDA is used as the coupling agent, absorbance may be measured in a range from 330–400 nm, with a peak around 350 nm. Alternatively, fluorescence may be measured with an excitation wavelength in a range from 240–400 nm, with a peak around 350 nm; and an emission wavelength in a range from 380–550 nm, with a peak around 430 nm.

The OPDA reaction is preferably performed for a period of about five minutes. After ascorbate oxidase is added, the rate of reaction is monitored by measuring absorbance at 350 nm, preferably for about five minutes. This rate of reaction is proportional to the amount of Vitamin C present in the sample.

Ascorbic acid is rapidly oxidized to DHAA in certain environments, such as in plasma. Metaphosphoric acid (MPA) and dithiothreitol (DTT) are added prior to analysis of the sample. The DTT reduces DHAA to ascorbic acid, and the MPA deproteinizes the sample to inhibit further oxidation. Neither the DTT nor the MPA should be present in a concentration high enough to interfere with either the ascorbate oxidase reaction or the OPDA reaction.

The use of MPA/DTT reduces DHAA in the sample to ascorbic acid, thereby stabilizing it. This feature is desirable, because "total Vitamin C" measurements are generally considered to be the sum of ascorbic acid and DHAA levels. (In vitro but not in vivo, DHAA is primarily a degradation product of ascorbic acid. Both forms are biologically active.) Samples should be stored with MPA/DTT at $-70°$ C. if not analyzed immediately. Samples which have thus been pretreated should not be re-treated with additional MPA/DTT before analysis. (Too much MPA/DTT can interfere with the reaction.)

Other than interference by excess MPA/DTT, no interferences to the novel method of assaying Vitamin C are known at this time. Most interferences in the sample should be corrected for by the blank reaction using OPDA but not ascorbate oxidase.

Preferred conditions are as follows: final concentrations of 0.4 g/L OPDA and 1.7 mg/L AO in pH 6.5 phosphate buffer; calibration using 5 and 20 mg/L aqueous ascorbic acid standards.

Linearity has been observed at least up to 200 mg/L ascorbic acid. Stabilization of a plasma sample may be achieved by adding 50 μl of metaphosphoric acid/dithiothreitol (400 g/L and 8.25 g/L, respectively) to 500 μl of heparinized plasma, followed by centrifugation. Samples may be stored for extended times at $-70°$ C. if treated with MPA/DTT. Recovery is 94% with a CV of 6% at 13.4 mg/L.

EXAMPLES

When blood is analyzed, heparinized plasma is the preferred sample. Blood is collected in a vacutainer tube, is mixed well, and is centrifuged immediately at 5° C. The plasma is decanted. If the sample is not to be analyzed immediately, it may be stored safely at $-70°$ C. in a cryovial after treatment with MPA/DTT as described below, and then thawed to room temperature at the time of analysis. The sample and controls are preferably not heated in a water bath or otherwise heated at an elevated temperature upon thawing.

Reagents are made from analytical grade reagents as follows:

Phosphate Buffer (0.1 mol/L, pH 6.5) 11.5470 grams of $NaH_2PO_4$ and 3.8853 grams of $Na_2HPO_4.7H_2O$ are dissolved in approximately 800 ml of deionized water in a 1000 ml beaker. With stirring, the pH is adjusted to 6.5 with hydrochloric acid or sodium hydroxide solution. The solution is transferred to a 1000 ml volumetric flask, and the flask is filled to the 1000 ml mark with deionized water. This buffer may be stored in a plastic bottle, and is stable for at least one year when kept at 4° C.

$NaH_2PO_4$—11.5470 g (0.8368 mol/L)

$Na_2HPO_4$—3.8853 g (0.1632 mol/L)

OPDA (0.5 g/L)—0.0500 g o-phenylenediamine dihydrochloride (Sigma, Catalog #P1526) (stored in a freezer) is transferred to a 100 ml volumetric flask, dissolved in the pH 6.5 phosphate buffer (above), and diluted to the 100 ml mark of a 100 ml volumetric flask with the pH 6.5 phosphate buffer. The solution is stored in an amber bottle at 4° C., where it is stable for at least one month. The solution should be checked after any storage period to verify quality control and stability.

Ascorbate Oxidase Stock Solution (1 mg/ml) 5.00 ml of deionized water are added to a vial containing 5.00 mg of ascorbate oxidase (Sigma, Catalog Number A0157, 1000 Units). (It is expected that other ascorbate oxidases will also work in the method of this invention.) After mixing well, 200 μl aliquots are placed in cryovials and stored at $-70°$ C.

Ascorbate Oxidase Working Solution (0.04 g/ml) One vial of the ascorbate oxidase stock solution is thawed. 4.8 ml of the pH 6.5 phosphate buffer is pipetted into a test tube. A small amount (1–1.5 ml) of the buffer is poured into the vial. The contents of the vial are mixed and transferred into the test tube containing the remaining buffer. This procedure is repeated several times until all of the ascorbate oxidase has been dissolved in the buffer. This solution is mixed well by inversion, and is transferred to a reagent cartridge. This solution is stable for at least one month. Calibration should be performed to verify quality control and stability.

MPA and DTT Solution, 400 g/L and 8.25 g/L, respectively. 4.0 g of metaphosphoric acid and 0.08250 g of dithiothreitol (Sigma, Catalog #D0632) are weighed, and both are transferred to a 50 ml beaker, where they are mixed with approximately 7 ml of deionized water. When dissolved, the contents are transferred to a 10 ml volumetric flask, which is then filled to the 10 ml mark with deionized water. Fresh MPA/DTT solution should be prepared each day of use.

Ascorbic Acid Standards

Stock 500 mg/L 0.0500 g of ascorbic acid is weighed and transferred to a 100 ml volumetric flask. The ascorbic acid is dissolved in a small amount of deionized water; 10 ml of the MPA/DTT solution is added, and the flask is filled to the 100 ml mark with deionized water. The solution is mixed well, and stored at 4° C. Alternatively, the stock solution can be made without MPA/DTT if the calibration standards are prepared immediately, and if the calibration standards are made with MPA/DTT.

Linearity and Calibration Solutions (100, 80, 60, 40, 20, 10, 5, and 2.5 mg/L) Into separate 10 ml volumetric flasks are pipetted the volumes of the 500 mg/L Stock Standard shown in the table below. 1.0 ml of MPA/DTT solution is added, and the flask is filled to the 10 ml mark with deionized water. The solutions are stored at 4° C. The 5 mg/L and 20 mg/L standards are preferably used for calibration.

| Concentration | Volume of Stock |
| --- | --- |
| 100 mg/L | 2.0 ml |
| 80 mg/L | 1.6 ml |
| 60 mg/L | 1.2 ml |
| 40 mg/L | 800 μl |

-continued

| Concentration | Volume of Stock |
|---|---|
| 20 mg/L | 400 µl |
| 10 mg/L | 200 µl |
| 5 mg/L | 100 µl |
| 2.5 mg/L | 50 µl |

Controls for Vitamin C are prepared from Bio Rad I (normal) and II (abnormal) Unassayed Serum Chemistry Controls (lyophilized, unassayed, pooled human serum chemistry control samples). Because there is little or no Vitamin C in these controls, the controls are spiked with Vitamin C, and treated with the MPA/DTT solution.

Two vials each of the Bio Rad I and II controls are reconstituted with 10 ml of deionized water for each vial. After the solutions are reconstituted, both vials of Level I are combined in a small beaker, and both vials of Level II are combined in another small beaker. 200 µl of the 500 mg/L ascorbic acid stock standard is added to the Level I beaker. 600 µl of the 500 mg/L ascorbic acid stock standard is added to the Level II beaker. Each beaker is mixed well. 5.0 ml of each Level is pipetted into 4 separate test tubes per level. To each test tube is added 500 µl of MPA/DTT solution. Each tube is vortexed and centrifuged for 10 minutes at 4000 rpm. The supernatant from each tube is pipetted into another test tube and filtered. A 500 µl aliquot of each filtrate is placed into cryovials for Levels I and II, which may be stored at −70° C. until used. When used, the controls should be thawed at room temperature. Thawing should preferably not be performed with a water bath or at an elevated temperature, which could cause proteins to precipitate, resulting in erroneous measurements. Quality control measurements should be performed each day of analysis to verify integrity of the reagents and of the procedures. These samples should not be re-treated with MPA/DTT, and may be analyzed directly.

For each sample to be analyzed, 500 µl of heparinized plasma is pipetted into a 10×75 test tube. 50 µl of MPA/DTT solution is added; the tube is vortexed well, and is then centrifuged at 3000 rpm for 10 minutes. The supernatant is pipetted into small cups for analysis. After calibration and quality control procedures have been completed, absorption at 350 nm is measured.

If a food, pharmaceutical, or vitamin supplement were the sample, the procedures described above for plasma could be followed, with the following modifications. The sample would initially be homogenized or blended with aqueous MPA/DTT solution, and then filtered or centrifuged. The assay would then be run on the supernatant. Depending on the concentration of Vitamin C in the sample, dilution may be appropriate before conducting the assay.

Tissues or blood constituents other than plasma may also be assayed in a manner analogous to that described above for a food sample.

I claim:

1. A method for assaying total Vitamin C in a sample wherein the Vitamin C is present as ascorbic acid, dehydroascorbic acid, or both; wherein the sample my also contain one or more proteins; wherein the sample may also contain one or more substances other than dehydroascorbic acid which will react with o-phenylenediamine to form a quinoxaline; and wherein the sample may also contain one or more substances which will interfere with the spectrometry of 3-(1,2-dihydroxyethyl)furo[3,4-b]quinoxaline-1-one; the method comprising the sequential steps of:

(a) first, reacting the sample with metaphosphoric acid and dithiothreitol, whereby the sample is deproteinized and whereby any dehydroascorbic acid in the sample is reduced to ascorbic acid;

(b) second, reacting the sample with o-phenylenediamine and then measuring the absorbance or fluorescence of the sample at a wavelength characteristic of 3-(1,2-dihydroxyethyl)furo[3,4-b]quinoxaline-1-one, whereby a blank measurement is made corresponding to any interfering quinoxalines and to any other spectrometric interferences that may then be present in the sample; and (c) third, reacting the sample with an ascorbate oxidase and measuring the increase, as compared to the blank measurement of any interfering quinoxalines and any other spectrometric interferences, in absorbance or fluorescence at the same wavelength; whereby ascorbic acid in the sample is oxidized to dehydroascorbic acid; whereby the resulting dehydroascorbic acid reacts with the o-phenylenediamine to form 3-(1,2-dihydroxyethyl)-furo[3,4-b]quinoxaline-1-one; and whereby the measured increase in the absorbance or fluorescence is a measure of the total Vitamin C in the sample.

2. The method of claim 1, wherein the sample comprises a tissue, blood, blood plasma, or another blood constituent.

3. The method of claim 1, wherein the sample comprises a food.

4. The method of claim 1, wherein the sample comprises a pharmaceutical preparation or a vitamin supplement.

5. The method of claim 1, wherein both of said steps of measuring absorbance or fluorescence comprise measuring absorbance at a wavelength within the range from about 330 nm to about 400 nm.

6. The method of claim 1, wherein both of said steps of measuring absorbance or fluorescence comprise measuring fluorescence with an excitation wavelength within the range from about 240 nm to about 400 nm, and with an emission wavelength within the range from about 380 nm to about 550 nm.

7. A method for assaying total Vitamin C in a sample wherein the Vitamin C is present as ascorbic acid, dehydroascorbic acid, or both; wherein the sample may also contain one or more proteins; wherein the sample may also contain one or more substances other than dehydroascorbic acid which will react with the coupling agent recited below to form a quinoxaline; and wherein the sample may also contain one or more substances which will interfere with the spectrometry of the quinoxaline product recited below; the method comprising the sequential steps of:

(a) first, reacting the sample with a deproteinizing agent and a reducing agent, until the sample is deproteinized and until any dehydroascorbic acid in the sample is reduced to ascorbic acid;

(b) second, reacting the sample with a coupling agent comprising a substituted or unsubstituted 1,2-diaminobenzene, and then measuring the absorbance or fluorescence of the sample at a wavelength characteristic of the quinoxaline product of the reaction of the coupling agent with dehydroascorbic acid, whereby a blank measurement is made corresponding to any interfering quinoxalines and to any other spectrometric interferences that may then be present in the sample; and (c) third, reacting the sample with an ascorbate oxidase and measuring the increase, as compared to the blank measurement of any interfering quinoxalines and any other spectrometric interferences, in absorbance or fluorescence at the same wavelength; whereby ascorbic acid in the sample is oxidized to dehydroascorbic acid; whereby the resulting dehydroascorbic acid reacts with the coupling agent to form a quinoxaline product; and whereby the measured increase in the absorbance or fluorescence is a measure of the total Vitamin C in the sample.

8. The method of claim 7, wherein the deproteinizing agent comprises metaphosphoric acid, trichloroacetic acid, sulfosalicylic acid, perchloric acid, oxalic acid, acetic acid, formic acid, or an ultrafilter.

9. The method of claim 7, wherein the reducing agent comprises dithiothreitol; glutathione; mercaptoethanol; cysteine; homocysteine; or 2,3-dimercapto-1-propanol.

10. The method of claim 7, wherein the coupling agent comprises 1,2-diaminobenzene; 1,2-diamino-4,5-dimethylbenzene; 1,2-diamino-4-methoxybenzene; or 1,2-diamino-4-ethoxybenzene.

11. The method of claim 7, wherein
(a) the deproteinizing agent comprises metaphosphoric acid, trichloroacetic acid, sulfosalicylic acid, perchloric acid, oxalic acid, acetic acid, formic acid, or an ultrafilter;
(b) the reducing agent comprises dithiothreitol; glutathione; mercaptoethanol; cysteine; homocysteine; or 2,3-dimercapto-1-propanol; and
(c) the coupling agent comprises 1,2-diaminobenzene; 1,2-diamino-4,5-dimethylbenzene; 1,2-diamino-4-methoxybenzene; or 1,2-diamino-4-ethoxybenzene.

12. The method of claim 7, wherein the sample comprises a tissue, blood, blood plasma, or another blood constituent.

13. The method of claim 7, wherein the sample comprises a food.

14. The method of claim 7, wherein the sample comprises a pharmaceutical preparation or a vitamin supplement.

* * * * *